United States Patent
Meister et al.

(10) Patent No.: US 8,374,699 B2
(45) Date of Patent: Feb. 12, 2013

(54) ENVELOPE SPECIFIC STIMULUS TIMING (75) Inventors: Dirk Meister, Axams (AT); Florian Frühauf, Rinn (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 13/171,953

(22) Filed: Jun. 29, 2011

(65) Prior Publication Data
US 2012/0004706 A1  Jan. 5, 2012

Related U.S. Application Data (60) Provisional application No. 61/360,123, filed on Jun. 30, 2010.

(51) Int. Cl.
*A61N 1/36* (2006.01)

(52) U.S. Cl. ................................. 607/57

(58) Field of Classification Search ........... 607/55–57, 607/136, 137
See application file for complete search history.

(56) References Cited

U.S. PATENT DOCUMENTS

| | | | |
|---|---|---|---|
| 6,480,820 B1 * | 11/2002 | Clopton et al. | 607/56 |
| 2007/0270949 A1 | 11/2007 | Paolini et al. | 623/10 |
| 2007/0282396 A1 | 12/2007 | Overstreet et al. | 607/57 |
| 2009/0125082 A1 | 5/2009 | Schleich | 607/57 |
| 2009/0161896 A1 | 6/2009 | Swanson et al. | 381/316 |
| 2009/0312820 A1 | 12/2009 | Nie et al. | 607/57 |

OTHER PUBLICATIONS

ISA/US Commissioner for Patents, International Search Report and Written Opinion, PCT/US 11/42307, date of Mailing Nov. 14, 2011, 10 pages.

* cited by examiner

*Primary Examiner* — George Evanisko
(74) *Attorney, Agent, or Firm* — Sunstein Kann Murphy & Timbers LLP (57) ABSTRACT

An implantable stimulation arrangement is described for generating electrode stimulation signals for an implanted electrode array having stimulation electrodes. A filter bank preprocessor processes an input acoustic audio signal to generate band pass signals each corresponding to an associated band of audio frequencies. A signal envelope module computes a corresponding signal envelope for each band pass signal. A stimulation pulse generator extracts stimulation signal information from the rate of change of the signal envelopes such as a time-based derivative to generate stimulation event signals defining electrode stimulation timings and amplitudes for some or all of the stimulation electrodes.

28 Claims, 11 Drawing Sheets

ENVELOPE SPECIFIC STIMULUS TIMING

This application claims priority from U.S. Provisional Patent Application 61/360,123, filed Jun. 30, 2010, incorporated herein by reference.

FIELD OF THE INVENTION

The present invention relates to cochlear implants, and specifically to the signal processing used therein.

BACKGROUND ART

Figure 1:
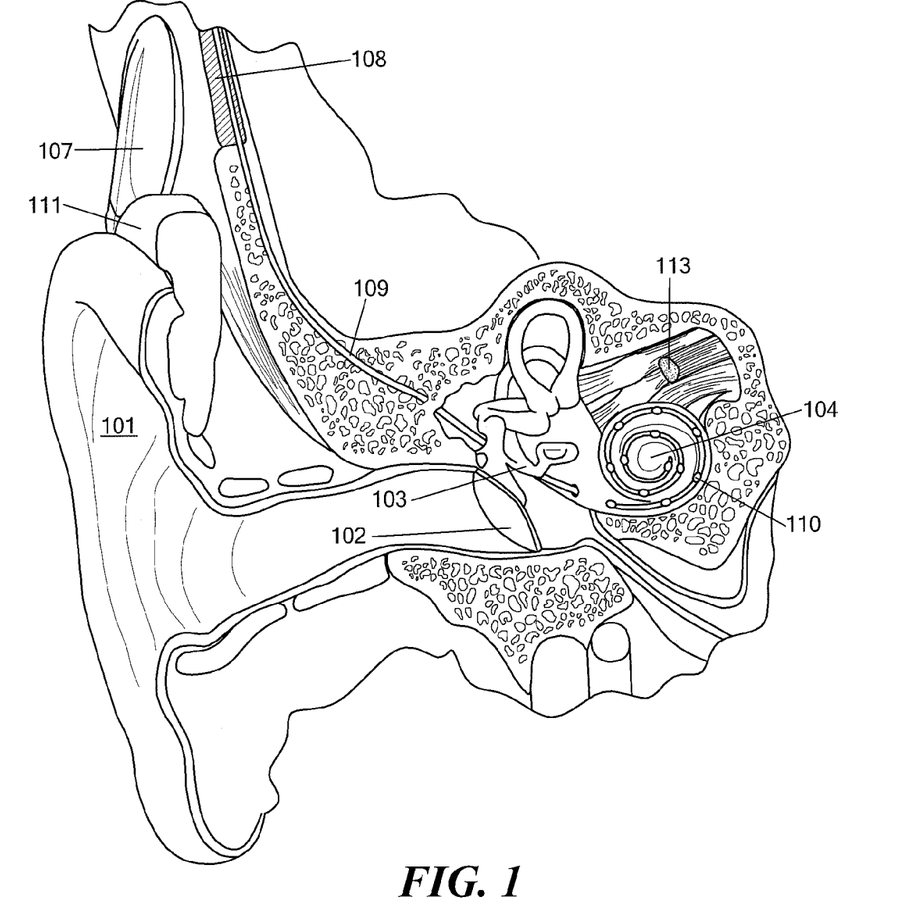
FIG. 1 shows a section view of the anatomy of a human ear containing a typical cochlear implant (CI) system.

A normal ear transmits sounds as shown in FIG. 1 through the outer ear 101 to the tympanic membrane (eardrum) 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system which includes an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple electrodes on its surface that provide selective stimulation of the cochlea 104.

In cochlear implants today, a relatively small number of electrodes are each associated with relatively broad frequency bands, with each electrode addressing a group of neurons through a stimulation pulse the charge of which is derived from the instantaneous amplitude of the envelope within that frequency band. In some coding strategies, stimulation pulses are applied at constant rate across all electrodes, whereas in other coding strategies, stimulation pulses are applied at an electrode-specific rate.

Various signal processing schemes can be implemented to produce the electrical stimulation signals. Signal processing approaches that are well-known in the field of cochlear implants include continuous interleaved sampling (CIS) digital signal processing, channel specific sampling sequences (CSSS) digital signal processing (as described in U.S. Pat. No. 6,348,070, incorporated herein by reference), spectral peak (SPEAK) digital signal processing, and compressed analog (CA) signal processing. For example, in the CIS approach, signal processing for the speech processor involves the following steps:

(1) splitting up of the audio frequency range into spectral bands by means of a filter bank,
(2) envelope detection of each filter output signal,
(3) instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals. These signals are sampled sequentially, and the stimulation pulses are applied in a strictly non-overlapping sequence. Thus, as a typical CIS-feature, only one stimulation channel is active at one time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit. Each output of the CIS band pass filters can roughly be regarded as a sinusoid at the center frequency of the band pass filter which is modulated by the envelope signal. This is due to the quality factor ($Q \approx 3$) of the filters. In case of a voiced speech segment, this envelope is approximately periodic, and the repetition rate is equal to the pitch frequency.

In the existing CIS-strategy, only the envelope signals are used for further processing, i.e., they contain the entire stimulation information. For each channel, the envelope is represented as a sequence of biphasic pulses at a constant repetition rate. A characteristic feature of CIS is that this repetition rate (typically 1.5 kpps) is equal for all channels and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually chosen at greater than twice the bandwidth of the envelope signals (Nyquist theorem).

Another cochlear implant stimulation strategy that transmits fine time structure information is the Fine Structure Processing (FSP) strategy by Med-El. Zero crossings of the band pass filtered time signals are tracked, and at each negative to positive zero crossing a Channel Specific Sampling Sequence (CSSS) is started. Typically CSSS sequences are only applied on the first one or two most apical channels, covering the frequency range up to 200 or 330 Hz. The FSP arrangement is described further in Hochmair I, Nopp P, Jolly C, Schmidt M, SchoBer H, Garnham C, Anderson I, *MED-EL Cochlear Implants: State of the Art and a Glimpse into the Future*, Trends in Amplification, vol. 10, 201-219, 2006, which is incorporated herein by reference.

It is known that existing stimulation strategies are imperfect. For example, CIS is known to be non-specific to some signal properties. FSP does provide fine structure information on some of the lower frequency channels, and CIS-like stimulation on the higher channels, but FSP strategies suffer from channel interactions that are enforced by an unbalanced rate-profile: a high rate is applied for CIS-channels, and low rates for FS channels. The pulse rate of CIS stimulation does not code information, only signal amplitude is coded via constant sampling of the signals envelope. In addition, electrical power consumption is relatively high. Moreover, CIS stimulation is not specific to auditory nerve properties: neurograms of auditory nerve tissues from cats show peaks that are synchronous to the fundamental frequency for high-frequency channels. See, e.g., Secker-Walker & Searle, *Time Domain Analysis Of Auditory Nerve Tissue Firing Rates*, J Acoust. Soc. Am., 88(3), 1990, p. 1427-1436; incorporated herein by reference. Currently only the FSP strategy uses irregular pulse rates, but only on the FS channels not the CIS channels.

U.S. Patent Application 20090161896 describes a method where pulse stimuli are generated at peaks of the band pass envelope based on rectified low-pass filtering. However, the stimulus timings are not based on physiological properties of auditory nerve tissues.

SUMMARY OF THE INVENTION

Embodiments of the present invention are directed to an implantable stimulation arrangement for generating electrode stimulation signals for an implanted electrode array having stimulation electrodes. A filter bank pre-processor processes an input acoustic audio signal to generate band pass signals each corresponding to an associated band of audio frequencies. A signal envelope module computes a corresponding signal envelope for each band pass signal. A stimulation pulse generator extracts stimulation signal information from the rate of change of the signal envelopes such as a time-based derivative to generate stimulation event signals defining electrode stimulation timings and amplitudes for some or all of the stimulation electrodes.

In some such embodiments, a pulse shaper may develop the stimulation event signals into output electrode pulses to the stimulation electrodes. An envelope filter may smooth and zero reference the signal envelopes computed by the signal envelope module, and the electrode stimulation timings may be defined based on the zero crossings of the zero referenced signal envelopes. The stimulation signal information may be extracted based on a time-based derivative such as a first, second or third order derivative. And the stimulation pulse generator may use a derivative threshold value to generate the stimulation event signals. At least some of the stimulation event amplitudes may be defined based on the maximum and/or minimum amplitude of the signal envelope. The signal envelope module may compute the signal envelope based on a Hilbert transformation, and/or based on rectification and filtering of the band pass signals.

The stimulation pulse generator may take into account physiological properties of auditory nerve tissue to generate the stimulation event signals. In addition or alternatively, a First Spike Latency (FSL) function may be used to generate the stimulation event signals. There may be a derivative threshold value used to generate the stimulation event signals. The stimulation pulse generator may define the electrode stimulation timings to provide an adaptive delay based on the rate of change of the signal envelope. Stimulation event signals may be generated for all of the stimulation electrodes based on the rate of change of the signal envelope. Or stimulation event signals for some of the stimulation electrodes may be based on a Fine Structure Processing (FSP) function.

The stimulation pulse generator may further weight the electrode stimulation amplitudes based on one or more signal features.

Embodiments of the present invention also include a similar method for generating electrode stimulation signals for an implanted electrode array having stimulation electrodes. An input acoustic audio signal is processed with a signal filter bank to generate band pass signals each corresponding to an associated band of audio frequencies. A corresponding signal envelope is computed for each band pass signal. Stimulation signal information is extracted based on the rate of change of the signal envelopes to generate stimulation event signals defining electrode stimulation timings and amplitudes for some or all of the stimulation electrodes.

In further such embodiments, the method may further include smoothing and zero referencing the signal envelopes for each band pass signal, and/or developing the stimulation event signals into output electrode pulses to the stimulation electrodes. The electrode stimulation timings may be defined based on the zero referenced signal envelopes. The stimulation signal information may be extracted based on a time-based such as a first, second or third order derivative. At least some of the electrode stimulation amplitudes may be defined based on maximum and/or minimum amplitude of the signal envelopes. Computing the signal envelopes may include using a Hilbert transformation, and/or rectification and filtering of the band pass signals.

Generating the stimulation event signals may further reflect physiological properties of auditory nerve tissue. The stimulation event signals may be generated using a First Spike Latency (FSL) function and/or a derivative threshold. Generating the stimulation event signals may include defining the electrode stimulation timings to provide an adaptive delay based on the rate of change of the signal envelope. The stimulation event signals may be generated for all of the stimulation electrodes based on the rate of change of the signal envelope. Or stimulation event signals may be generated for some of the stimulation electrodes based on a Fine Structure Processing (FSP) function. Generating the stimulation event signals may also include weighting the electrode stimulation amplitudes based on one or more signal features.

DETAILED DESCRIPTION OF SPECIFIC EMBODIMENTS

Various embodiments of the present invention are directed to an improved approach for signal processing in a cochlear implant system where the stimulus timings and amplitudes are adapted to the envelope of each channel's band pass signal. Then points in time and amplitudes that are important for neural coding are selected for stimulating.

The presentation of the fundamental frequency of an audio signal also is improved. Unresolved harmonics of the fundamental frequency can be contained in a signal channel if the bandwidth of the channel is greater than the fundamental frequency. When two or more harmonics are contained in a frequency band, then they are called unresolved harmonics, which lead to a beating frequency of the signals envelope in this channel, with a beating frequency that is dominated by the fundamental frequency. Embodiments of the present invention apply pulses with a pulse rate that is correlated to the fundamental frequency in channels with unresolved harmonics.

In a specific embodiment, the electrode stimulation timings and amplitudes can be defined based on a First Spike Latency (FSL) function which is connected to the second order derivatives of the band pass signal envelopes. See, e.g., P. Heil, *Auditory Cortical Onset Responses Revisited: I. First-Spike Timing*, J. Neurophysiol. 77, 2616-2641 (1997); incorporated herein by reference. FSL timing of auditory nerve fibers is a function of peak pressure which in turn is equivalent to the second derivative of the signal envelope. FSL appears to be a better parameter than spike counts in evaluation of the response of a neuron to frequency and amplitude in mouse inferior colliculus. See, e.g., Tan et al., *First Spike Latency And Spike Count As Functions Of Tone Amplitude And Frequency In The Inferior Colliculus Of Mice*, Hear Res. 235(1-2): 90-104, 2008; incorporated herein by reference. FSL also probably carries most of the location-related information present in spike patterns. See., e.g., Furukawa et al., *Cortical Representation of Auditory Space: Information-Bearing Features of Spike Patterns*, J. of Neurophysiology, Vol. 87 No. 4 April 2002, pp. 1749-1762; incorporated herein by reference. A signal processing approach based on FSL computes points in time where the third order derivative of the signal envelope, filtered with the second band pass, has negative to positive zero-crossings. At these points, the second order derivative of the signal envelope reaches its minimum value. At these points in time stimulation pulses could be applied.

Figure 2:
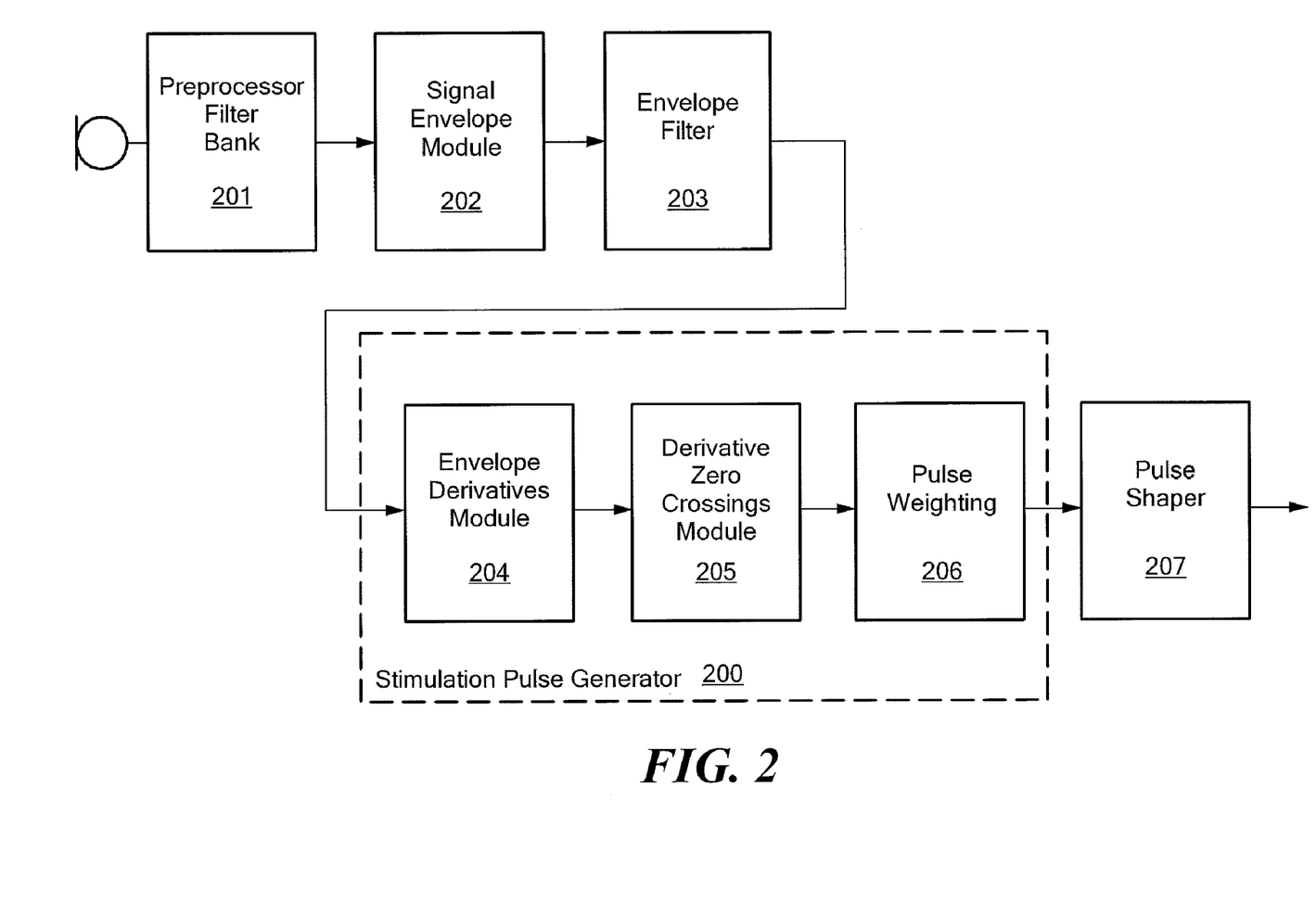
FIG. 2 shows major functional blocks in the signal processing arrangement of one specific embodiment of the present invention.

FIG. 2 shows major functional blocks in a signal processing arrangement of a cochlear implant (CI) system according to one specific embodiment of the present invention. Preprocessor Filter Bank 201 is a bank of parallel signal filters that pre-processes an initial acoustic audio signal developed by a microphone. Each band pass filter in the Preprocessor Filter Bank 201 is associated with a specific band of audio frequencies so that the input acoustic audio signal is filtered into some N band pass signals, $B_1$ to $B_N$ where each band pass signal corresponds to the band of frequencies for one of the band pass filters.

Figure 3:
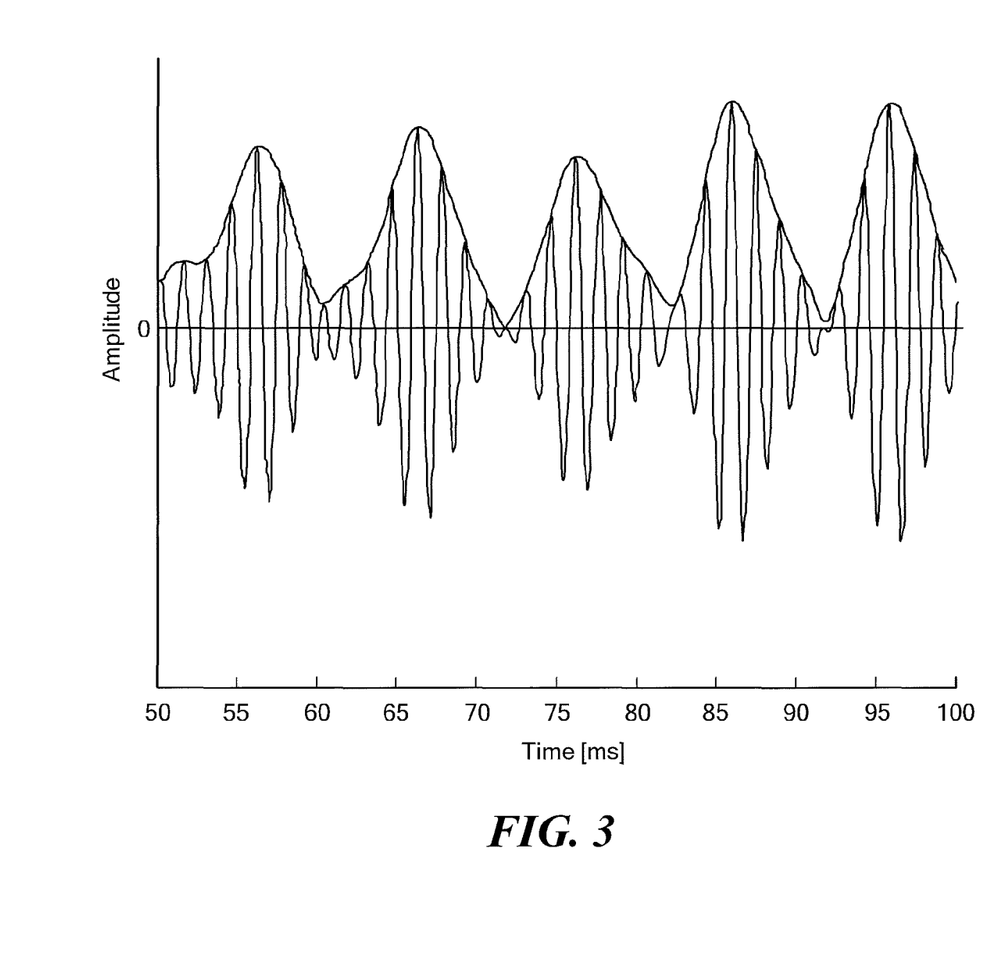
FIG. 3 shows an example of a band pass signal (dark line) and its corresponding signal envelope (light line).

The signals $B_1$ to $B_N$ are input to a Signal Envelope Module 202 that processes them into a corresponding signal envelope, which may be computed, for example, by Hilbert transformation or half-wave or full-wave rectification and low-pass filtering. FIG. 3 shows one specific example of 50 milliseconds of the band pass filtered time signal of the syllable "aba" from the Preprocessor Filter Bank 201, and the corresponding signal envelope as computed by the Signal Envelope Module 202 with the Hilbert transformation. The lower frequency boundary is about 490 Hz and the upper frequency boundary is about 710 Hz.

Figure 4:
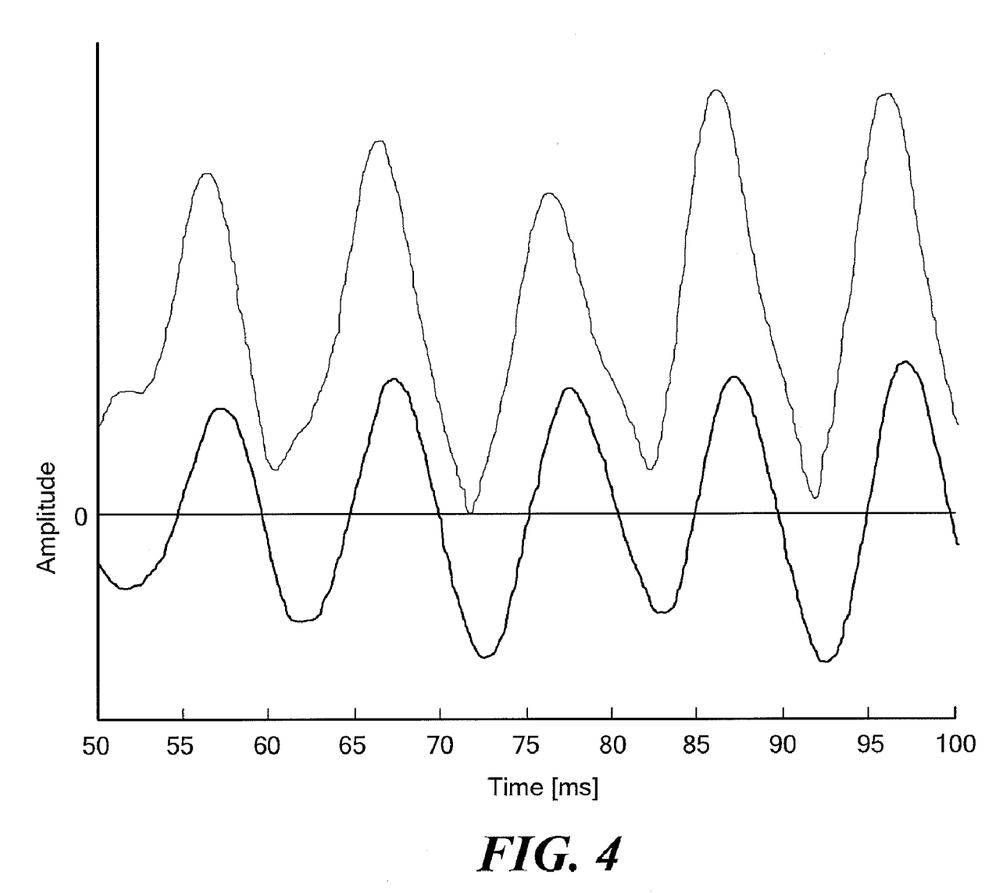
FIG. 4 shows an example of the envelope signal (light line) and the further band pass filtered envelope signal (dark line).

The signal envelopes are filtered by an Envelope Filter 203 to restrict the modulations in the signal envelopes to reasonable values and to derive a signal that oscillates around the zero level. FIG. 4 shows the signal envelope from the Signal Envelope Module 202 and the example of FIG. 3 (upper trace) and the resulting band pass filtered version of this same envelope (lower trace) as produced by the Envelope Filter 203. Reasonable filter cut-off frequencies for the Envelope Filter 203 would be the lowest cut-off frequency of the Preprocessor Filter Bank 201 and the bandwidth of the corresponding frequency band. Channel bandwidth reflects the maximum beating frequency that could result from two or more simultaneous frequencies in a given signal channel and is dominated by the frequency difference between the two frequencies in that channel. The maximum difference in frequency that is possible in one channel is the difference of its cut-off frequencies, which is equivalent to the channel bandwidth. The lower frequency of this band pass filtered envelope is about 100 Hz (e.g. the lowest cut-off frequency of the filter bank) and the upper frequency is set to the bandwidth of the corresponding filter band, e.g., here about 220 Hz. Choosing the cut-off frequency this way can bring out any frequency modulation due to unresolved harmonics that lie in the corresponding signal band. This envelope filtering operation of the Envelope Filter 203 creates a slight delay between the original signal envelope and the corresponding filtered envelope which is visible in FIG. 4. In some embodiments, it may be useful to introduce a delay compensation factor into the signal computations, an exercise which we omit here.

A Stimulation Pulse Generator 200 extracts stimulation signal information from the filtered signal envelopes to generate stimulation event signals $S_1$ to $S_N$ that define electrode stimulation timings and amplitudes for at least some of the stimulation electrodes based on the rate of change of the signal envelope for each corresponding band pass signal, for example, a time-based derivative.

Figure 5:
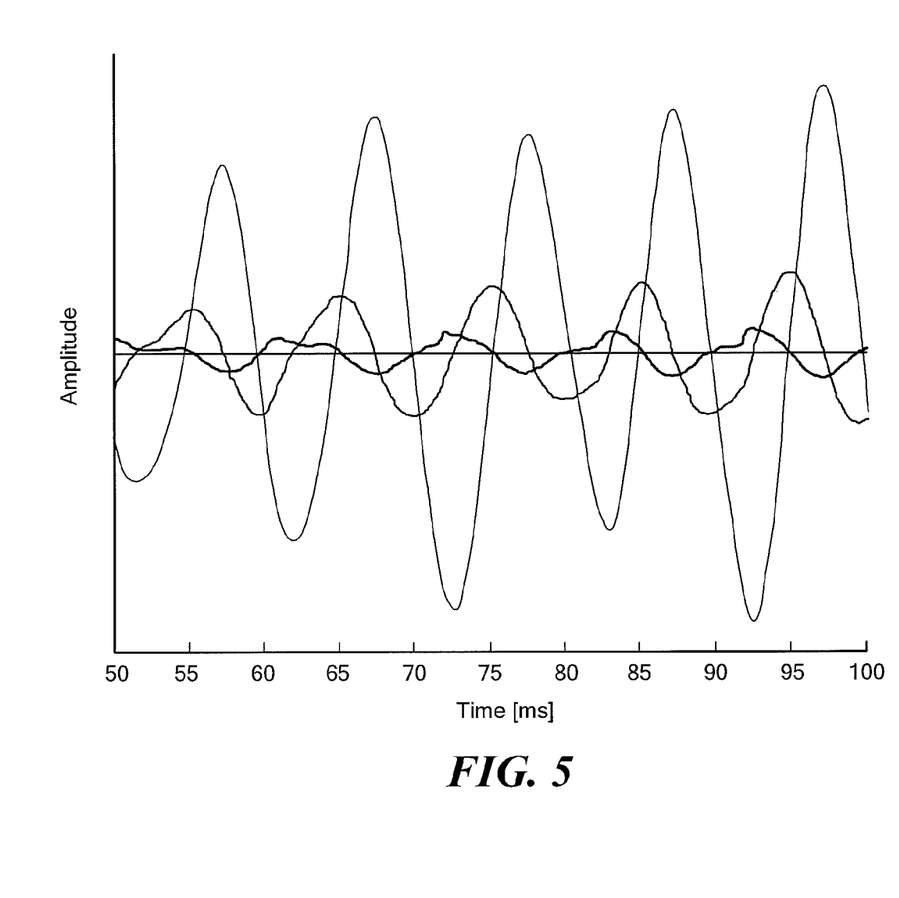
FIG. 5 shows the first and second order derivatives of the band pass filtered signal envelope.

More specifically, within the Stimulation Pulse Generator 200 an Envelope Derivates Module 204 computes time-based derivatives of any order from the filtered signal envelopes. FIG. 5 shows the filtered envelope from the Envelope Filter 203 using the previous examples (the larger sinusoidal trace), and the corresponding derivatives of that signal. The smaller sinusoidal trace represents the first order derivative, and the smallest irregular trace shows the second order derivative. (The derivatives are scaled for better illustration.) The Envelope Derivates Module 204 can compute the derivatives, for example, by subtracting succeeding values of the filtered signal envelopes.

Derivative Zero Crossings Module 205 determines negative to positive zero-crossings for the third order derivative. Actual calculation of the third order derivative zero-crossings can be avoided by using the first order derivative of the envelope signals. For sinusoid signals, zero-crossings of the first order derivative coincide to a good approximation with the zero-crossings of the third derivative. In FIG. 5 it can be seen that the peaks of the second order derivative nearly coincide with zero-crossings of the first order derivative. These minima of the second derivatives of the filtered signal envelope are referred to herein as "signal special extreme values."

Figure 6:
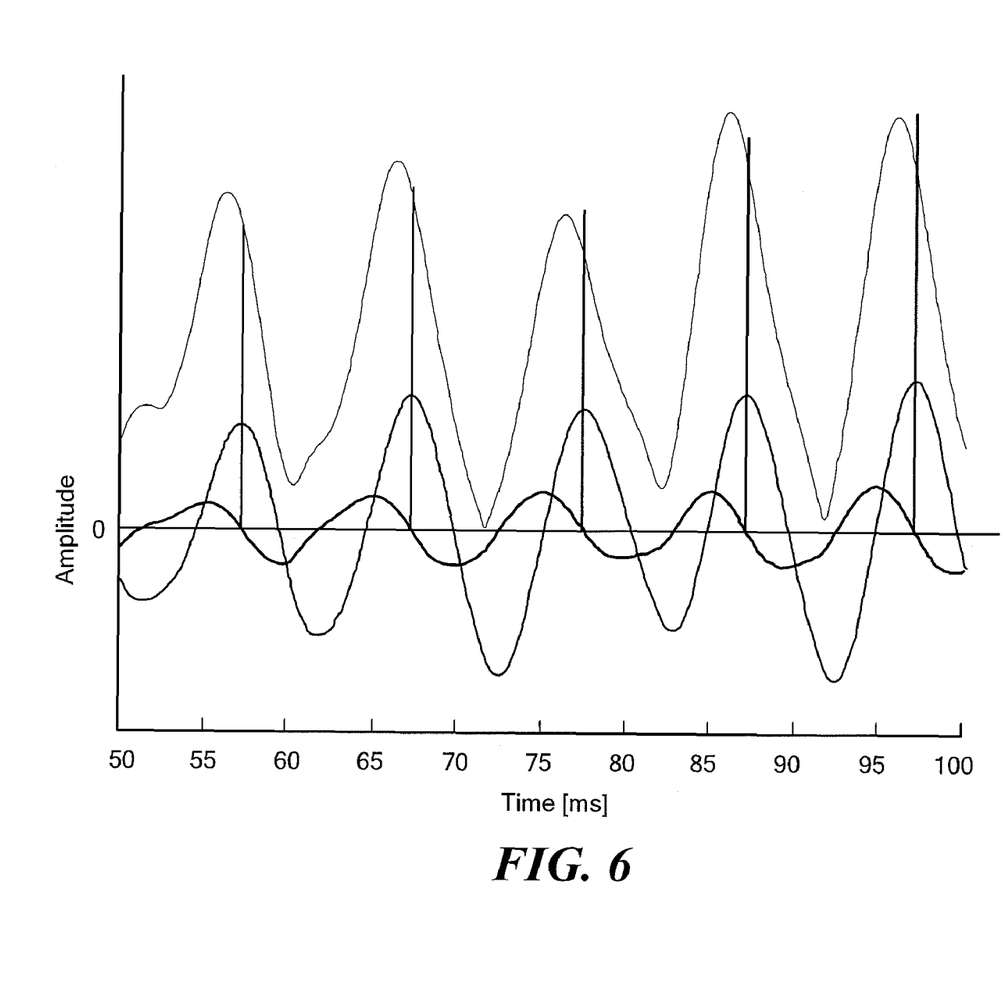
FIG. 6 shows pulses that are timed and weighted based on the 2nd derivative signals of the filtered signal envelope.

The Pulse Weighting Module 206 generates timings for stimulation event signals $S_1$ to $S_N$ based on the times of the zero crossings of the selected derivative and weights the amplitudes of the corresponding pulses based on the amplitude of the second order derivative of the filtered signal envelope at the corresponding point in time. FIG. 6 shows examples of the event timing pulses that are created by the Pulse Weighting Module 206 at the positive to negative zero-crossings of the first order derivative of the filtered signal envelopes. The Pulse Weighting Module 206 weights the timing pulses in FIG. 6 based on the amplitude of the second order derivative of the filtered signal envelope and scales by a negative constant factor.

Figure 7:
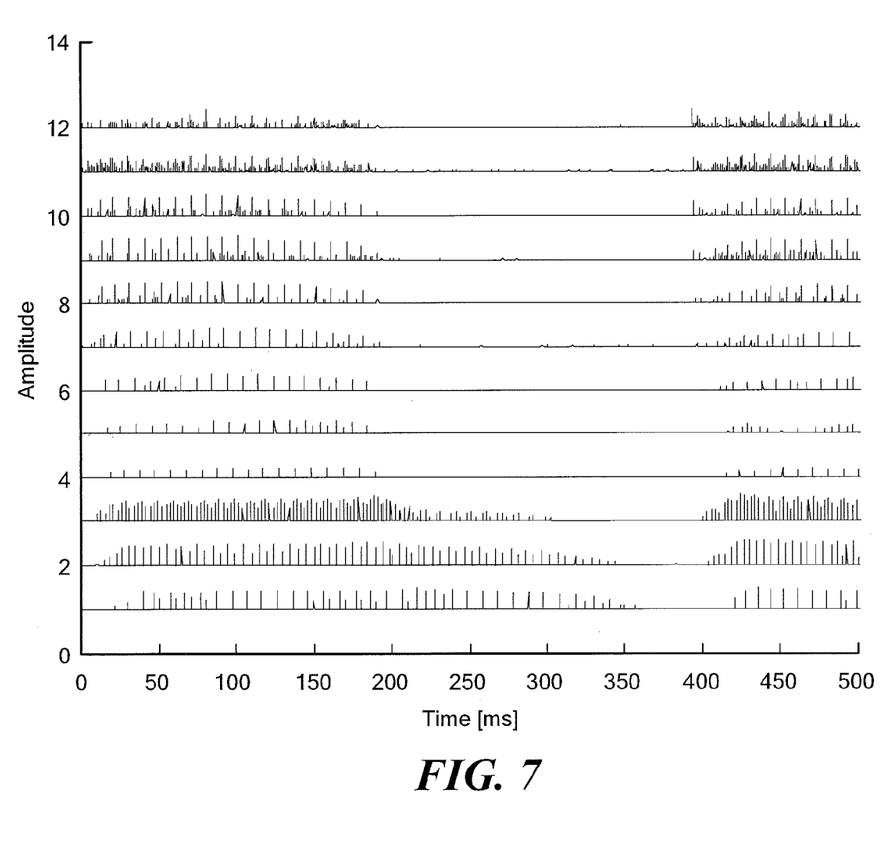
FIG. 7 a set of stimulations pulses as developed by a system using an embodiment of the present invention.

Pulse Shaper 207 develops the stimulation event signals $S_1$ to $S_N$ from the Pulse Weighting Module 206 into output electrode pulses $E_1$ to $E_M$ to the electrodes in the implanted electrode array to stimulate the adjacent nerve tissue. More specifically, the Pulse Shaper 207 scales template pulse shapes (e.g. biphasic pulses) with the produced stimulation event signals for output as electrode stimulation pulses to the stimulation electrodes. For example, FIG. 7 shows the applied stimuli for a 12 channel electrode. In FIG. 7, Channels 1-3 are processed similar to FSP with pulses at zero-crossings of the band pass time-signal, and Channels 4-12 are processed as described above based on FSL. The Channels 1-3 are lower frequency channels that were not selected for FSL processing as described above because their bandwidth is too low to contain unresolved harmonics of an average human speaker.

Figure 8:
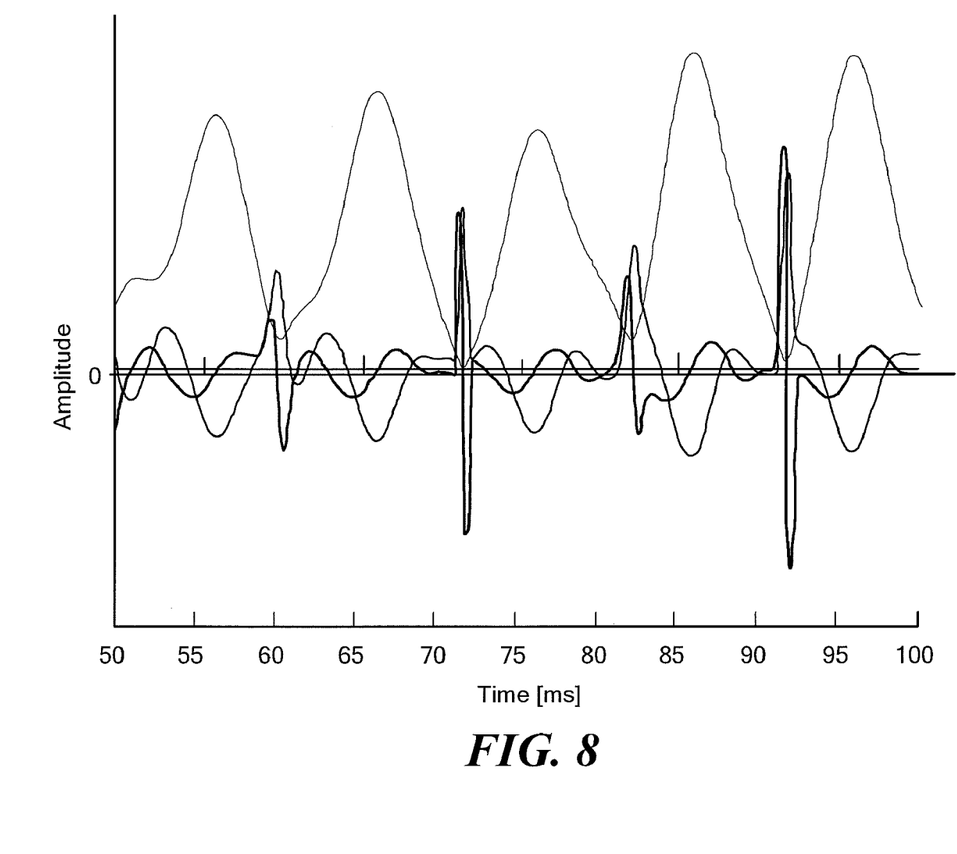
FIG. 8 shows an example of developing pulses based on one specific embodiment of the present invention, without the second band pass filter of the signal envelope.

In an alternative embodiment, the channel processing may be a variation of the approach described above without an Envelope Filter 203, but instead using a derivative threshold to determine the special extreme values. FIG. 8 shows an example of stimulation event signal pulses developed in this manner, where the uppermost gray trace is the band-pass signal envelope shown in FIG. 3 and its second and third order derivatives are computed. In FIG. 8, the second order derivative starts above zero at time 50 ms, whereas the third order derivative starts below zero at that time. Note, that in FIG. 8, these derivatives are scaled with a constant factor. The vertical black bars show where stimulation event signal pulses are created at the negative to positive zero-crossings of the third order derivative where the second order derivative has values below a certain threshold. These positions in time again are called the "special extreme values." As in the previous discussion, the size of the pulses is determined by the amplitude of the second order derivative scaled by a negative constant factor. One advantage of this approach as compared to the first is that no time delay arises due to a band-pass envelope filter, and that is why a threshold is introduced and used to filter out the special extreme values.

Figure 9:
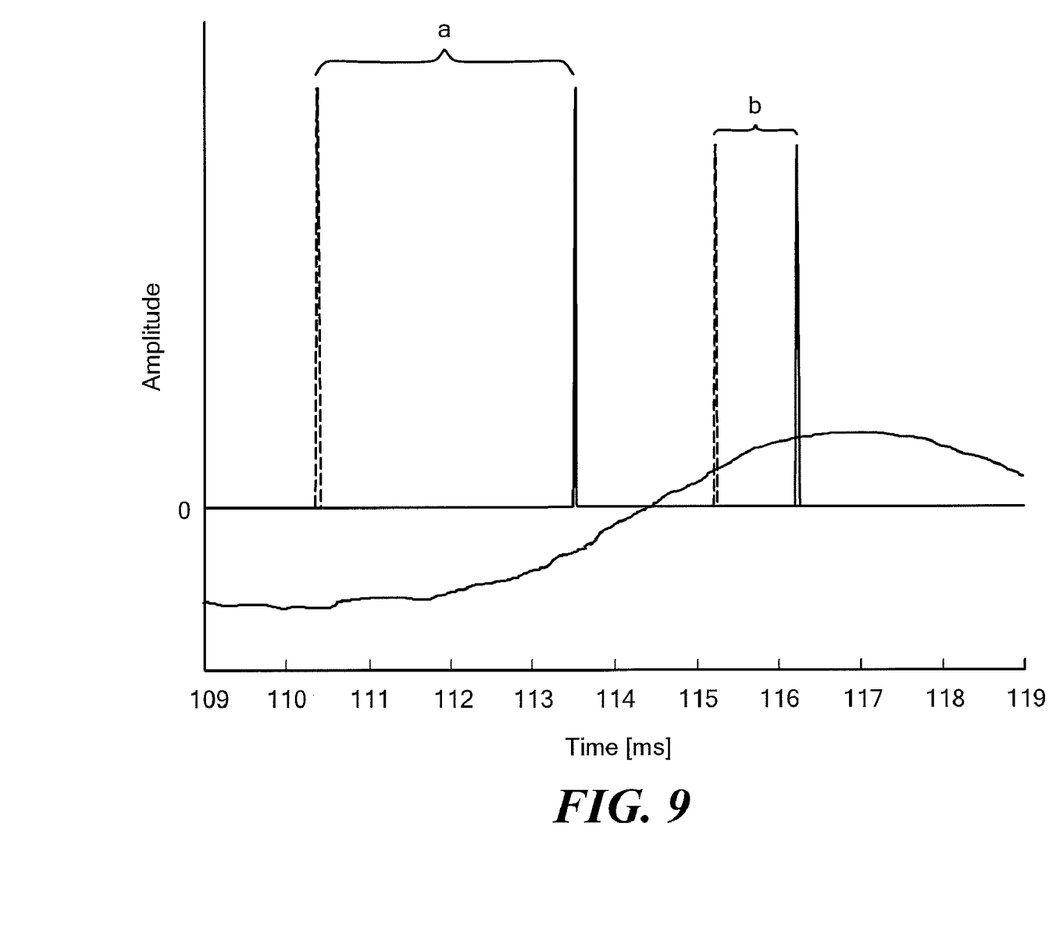
FIG. 9 shows an example of FSP pulses produced based on adaptive stimulus timing according to an embodiment of the present invention.

Another method to take the physiology of FSL into account for stimulation of the auditory nerve is based on computing the delays from a function that resembles FSL, and to apply this delay to the stimulation event signal pulses. These delays could be applied to any coding strategy that uses irregular timing for the stimulation event signal pulses, e.g. the FSP coding strategy. Each time a stimulation event signal pulse is identified, the second derivative of the signal amplitude at the time instance of this pulse is determined With the value of the second derivative and a FSL function, a signal adaptive delay can be computed and the respective pulse can be delayed by this adaptive delay. For example, the FSL function could be an approximation of the formula presented in Heil P., *Auditory Cortical Onset Responses Revisited. I. First-Spike Timing*, J. Neurophysiol. 77, 2616-2641, 1997 (incorporated herein by reference):

$$L_{CRF} = L_{min} + A_{CRF} * (\log APP_{max} + S)^{-\alpha}$$

where $L_{CRF}$ is the adaptive spike delay, $L_{min}$ is an independent delay, $APP_{max}$ is the maximum acceleration of peak pressure (second derivative of the signal envelope), $A_{CRF}$ is a scaling factor, and S is the neuron's transient sensitivity, a function of stimulation site (electrode). Instead of this specific FSL function, an approximation of the function also could be used, e.g. based on a 1/x function. And to speed up computing during signal processing, a lookup table could be used to determine the delay values from the signal envelope. FIG. 9 shows an example of this adaptive stimulus event signal pulse timing displaying the lowest in frequency channel (100-200 Hz) of a FSP strategy showing the FSP pulses in dashed lines and the delayed pulses in solid lines. The continuous curve represents the second derivative in time of the band pass filtered signal envelope. At points in time where the second derivative has low values, the delay between FSP stimulation event signal pulses and delayed stimulation event signal pulses is large, while at points in time where the second derivative has high values, the delay is small.

In some embodiments, the computed stimulation event signal pulses could be additionally weighted with other signal features, e.g. the signal envelope. And in some embodiments, rather than detecting zero-crossings of the first order or third order derivative, peaks of the second order derivative could be determined by holding the minimum value of the second derivative between two zero-crossings of the second derivative, which would then allow the second zero-crossing to be used for the pulse timing. And instead of features of the second order derivative of the signal envelope, other order derivatives could be used.

Figure 10:
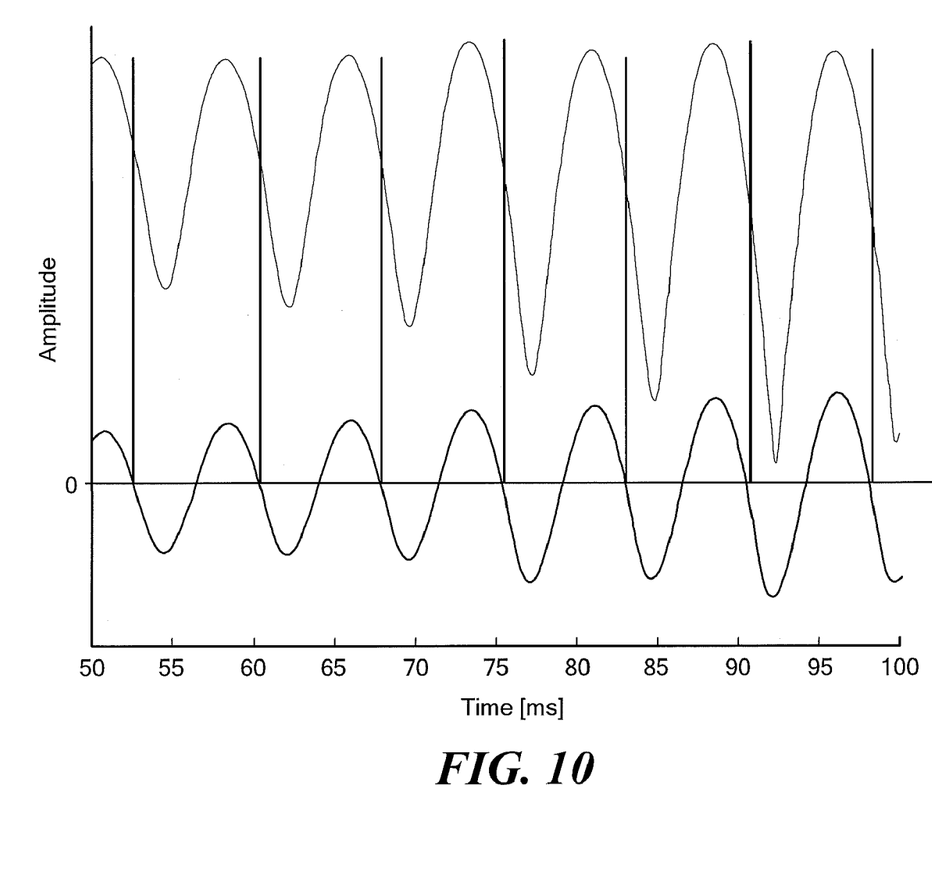
FIG. 10 shows an example of basing the electrode stimulation timings and amplitudes on the filtered signal envelope itself.

Another embodiment may base the electrode stimulation timings and amplitudes on the filtered signal envelope itself rather than a time-based derivative as such. In FIG. 10, the upper gray curve is the original band pass signal envelope, the lower dark curve is the smoothed (filtered) and zero referenced signal envelope, and the vertical black bars are the calculated stimulation event signal pulses which in this embodiment are generated at each positive-to-negative zero-crossing of the filtered signal envelope. Here the stimulation event (pulse) amplitude is defined based on the maximum amplitude value of the original signal envelope which appeared since the last zero-crossing.

Figure 11:
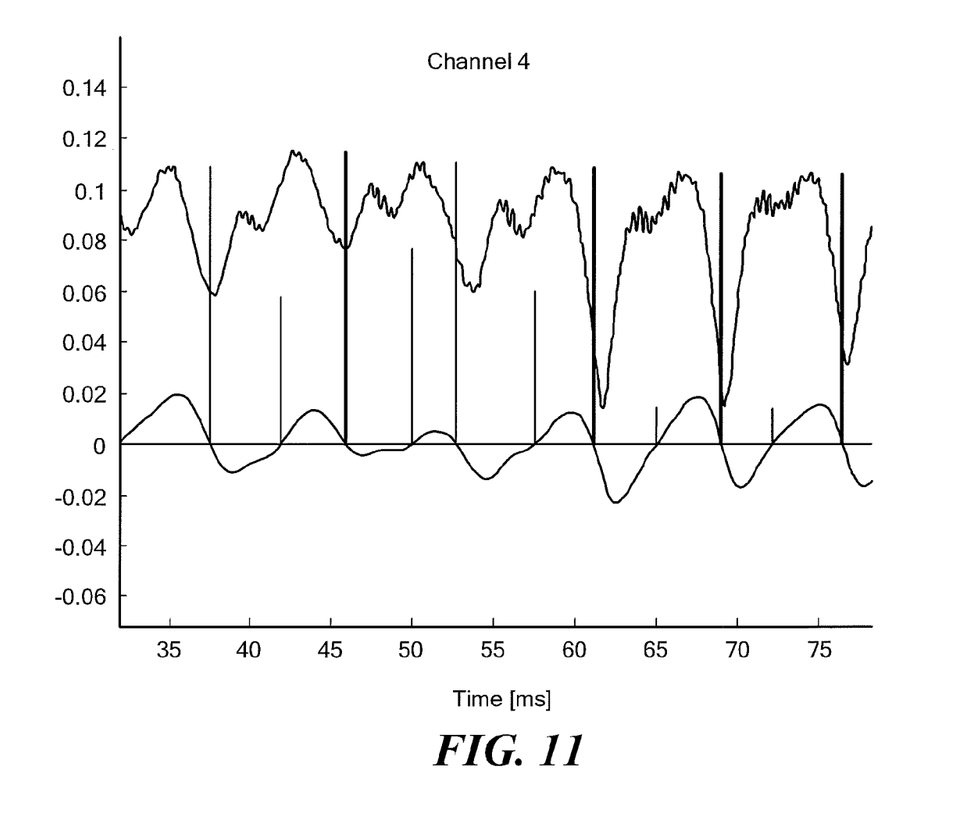
FIG. 11 shows an example where the stimulation event signal pulses are defined at every zero crossing of the filtered signal envelope.

FIG. 11 shows waveform signals used in another related embodiment where the stimulation even (pulse) amplitudes are defined based on the minimum values of the original (unfiltered) signal envelope (again, the upper gray waveform trace) where the pulse amplitudes are defined based on the minimum and maximum amplitudes of the signal envelope and applied at zero-crossings of the filtered signal envelope (the lower dark waveform trace). Note that in this embodiment, the stimulation event signal pulses are defined at every zero crossing of the filtered signal envelope, both the positive-to-negative zero crossings as in FIG. 10, and the negative-to-positive crossings, too. In this specific embodiment, the stimulation event signal pulses created on the negative-to-positive zero crossings have amplitudes based on the minima of the filtered signal envelope between negative-to-positive crossings of the signal envelope.

Compared to previous stimulation strategies such as CIS and FSP, embodiments of the present invention offer lower power consumption for cochlear stimulation due to fewer stimulation pulses being used. In addition, channel interactions are reduced due to the significantly lower number of applied pulses. Similar rates of stimulation are applied on all signal channels resulting in a smooth rate-profile. And a stronger presentation of envelope-ITDs occurs since most location-related information is coded in the latency of first-spike timing.

Embodiments of the invention may be implemented in whole or in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable stimulation arrangement for generating electrode stimulation signals for an implanted electrode array having a plurality of stimulation electrodes, the arrangement comprising:
    a filter bank pre-processor for processing an input acoustic audio signal, the pre-processor generating a plurality of band pass signals each corresponding to an associated band of audio frequencies;
    a signal envelope module for computing a corresponding signal envelope for each band pass signal; and
    a stimulation pulse generator for extracting stimulation signal information as a function of rate of change of the signal envelopes, the generator generating stimulation event signals based on the rate of change and defining electrode stimulation timings and amplitudes for a plurality of the stimulation electrodes.

2. An arrangement according to claim 1, further comprising:
    a pulse shaper for developing the stimulation event signals into output electrode pulses to the stimulation electrodes.

3. An arrangement according to claim 1, further comprising:
    an envelope filter for smoothing and zero referencing the signal envelopes computed by the signal envelope module.

4. An arrangement according to claim 3, wherein the electrode stimulation timings are defined based on zero crossings of the zero referenced signal envelopes.

5. An arrangement according to claim 1, wherein the rate of change of the signal envelopes includes a time-based derivative of the signal envelope.

6. An arrangement according to claim 5, wherein the stimulation pulse generator uses a derivative threshold value of the time-based derivative for extracting stimulation signal information as a function of rate of change of the signal envelopes.

7. An arrangement according to claim 1, wherein the stimulation pulse generator defines at least some of the electrode stimulation amplitudes based on maximum amplitude of the signal envelope.

8. An arrangement according to claim 1, wherein the signal envelope module performs rectification and filtering of the band pass signals for computing the signal envelope.

9. An arrangement according to claim 1, wherein the stimulation pulse generator takes into account physiological properties of auditory nerve tissue to generate the stimulation event signals.

10. An arrangement according to claim 1, wherein the stimulation pulse generator uses a First Spike Latency (FSL) function to generate the stimulation event signals.

11. An arrangement according to claim 1, wherein an adaptive delay based on the rate of change of the signal envelopes is provided when the stimulation pulse generator defines the electrode stimulation timings.

12. An arrangement according to claim 1, wherein the stimulation pulse generator generates stimulation event signals for all of the stimulation electrodes based on the rate of change of the signal envelopes.

13. An arrangement according to claim 1, wherein the stimulation pulse generator also generates stimulation event signals for some of the stimulation electrodes based on a Fine Structure Processing (FSP) function.

14. An arrangement according to claim 1, wherein on one or more signal features are used for weight the electrode stimulation amplitudes defined by the stimulation pulse generator.

15. A method for generating electrode stimulation signals for an implanted electrode array having a plurality of stimulation electrodes, the method comprising:
    processing an input acoustic audio signal with a signal filter bank and generating from the processing a plurality of band pass signals each corresponding to an associated band of audio frequencies;
    computing a corresponding signal envelope for each band pass signal; and
    extracting stimulation signal information as a function of rate of change of the signal envelopes and generating, based on the rate of change, stimulation event signals defining electrode stimulation timings and amplitudes for a plurality of the stimulation electrodes.

16. A method according to claim 15, further comprising:
developing the stimulation event signals into output electrode pulses to the stimulation electrodes.

17. A method according to claim 15, further comprising:
smoothing and zero referencing the signal envelopes for each band pass signal.

18. A method according to claim 17, wherein the electrode stimulation timings are defined based on zero crossings of the zero referenced signal envelopes.

19. A method according to claim 15, wherein the rate of change of the signal envelopes includes a time-based derivative of the signal envelope.

20. A method according to claim 19, wherein generating the stimulation event signals uses a derivative threshold value of the time-based derivative.

21. A method according to claim 15, wherein computing the signal envelopes includes using a Hilbert transformation.

22. A method according to claim 15, wherein computing the signal envelopes includes rectification and filtering of the band pass signals.

23. A method according to claim 15, wherein generating the stimulation event signals further reflects physiological properties of auditory nerve tissue.

24. A method according to claim 15, wherein generating the stimulation event signals uses a First Spike Latency (FSL) function.

25. A method according to claim 15, wherein defining the electrode stimulation timings includes providing an adaptive delay based on the rate of change of the signal envelopes.

26. A method according to claim 15, wherein the stimulation event signals are generated for all of the stimulation electrodes based on the rate of change of the signal envelopes.

27. A method according to claim 15, wherein the stimulation event signals are generated for some of the stimulation electrodes based on a Fine Structure Processing (FSP) function.

28. A method according to claim 15, wherein generating the stimulation event signals includes weighting the electrode stimulation amplitudes based on one or more signal features.

* * * * *

UNITED STATES PATENT AND TRADEMARK OFFICE
CERTIFICATE OF CORRECTION

| | |
|---|---|
| PATENT NO. | : 8,374,699 B2 |
| APPLICATION NO. | : 13/171953 |
| DATED | : February 12, 2013 |
| INVENTOR(S) | : Dirk Meister et al. |

It is certified that error appears in the above-identified patent and that said Letters Patent is hereby corrected as shown below:

In the Claims:

In Col. 10, line 51
replace "weight"
with --weighting--

Signed and Sealed this
Twenty-first Day of May, 2013

Teresa Stanek Rea
*Acting Director of the United States Patent and Trademark Office*